US008309780B2

(12) United States Patent
Dakka et al.

(10) Patent No.: US 8,309,780 B2
(45) Date of Patent: Nov. 13, 2012

(54) PROCESS FOR MAKING OLEFIN OLIGOMERS AND ALKYL BENZENES IN THE PRESENCE OF MIXED METAL OXIDE CATALYSTS

(75) Inventors: Jihad Mohammed Dakka, Whitehouse Station, NJ (US); Jeffrey T. Elks, Geneva, IL (US); James C. Vartuli, West Chester, PA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 713 days.

(21) Appl. No.: 12/005,027

(22) Filed: Dec. 21, 2007

(65) Prior Publication Data

US 2009/0163608 A1    Jun. 25, 2009

(51) Int. Cl.
C07C 2/10 (2006.01)
C07C 2/66 (2006.01)

(52) U.S. Cl. ........ 585/530; 585/502; 585/520; 585/532; 585/533; 585/446; 585/467

(58) Field of Classification Search .................. 585/520, 585/530, 532, 533, 446, 447, 502, 467
See application file for complete search history.

(56) References Cited

U.S. PATENT DOCUMENTS

| | | | | |
|---|---|---|---|---|
| 2,692,258 A | * | 10/1954 | Roebuck et al. | 526/96 |
| 3,778,365 A | | 12/1973 | Hamner et al. | |
| 3,909,394 A | | 9/1975 | Hayes | |
| 3,948,804 A | | 4/1976 | Rausch | |
| 4,367,137 A | | 1/1983 | Antos et al. | |
| 4,827,073 A | * | 5/1989 | Wu | 585/530 |
| 4,835,331 A | * | 5/1989 | Hammershaimb et al. | 585/520 |
| 5,146,030 A | * | 9/1992 | Sanderson et al. | 585/533 |
| 5,396,011 A | * | 3/1995 | Kuhn | 585/455 |

(Continued)

FOREIGN PATENT DOCUMENTS

WO    WO 2004067586 A2    8/2004

(Continued)

OTHER PUBLICATIONS

Bahrmann, et. al., "Oxo Synthesis" in Ullmann's Encyclopedia of Chemical Technology, Wiley-VCH, 2005, posted on-line Jun. 15, 2000.*

(Continued)

*Primary Examiner* — In Suk Bullock
*Assistant Examiner* — Bradley Etherton
(74) *Attorney, Agent, or Firm* — Robert A. Migliorini

(57) ABSTRACT

Provided is a process for oligomerizing n-olefins. The process has the step of reacting (oligomerizing) an amount of one or more n-olefins in the presence of a catalytically effective amount of a two or more metal oxides at a temperature effective to effect oligomerization. The two or more metal oxides are represented by the formula $MO_n/M'O_{n'}$. M and M', are, independently, selected from the group consisting of Al, Ce, Fe, P, W, Zr, and combinations thereof. M and M' are different metals or combinations of metals. "n" and "n'" are positive numbers and vary stoichiometrically depending on the valency of M and M', respectively. Provided is also a process for alkylation of an alkylatable aromatic compound. The process has the step of contacting an amount of one or more n-olefins with an amount of aromatic compound in the presence of a catalytically effective amount of the two or more metal oxides at a temperature effective to effect alkylation of the aromatic compound.

25 Claims, 4 Drawing Sheets

U.S. PATENT DOCUMENTS

| | | | |
|---|---|---|---|
| 5,453,556 A * | 9/1995 | Chang et al. | 585/524 |
| 5,563,311 A * | 10/1996 | Chang et al. | 585/467 |
| 5,608,133 A * | 3/1997 | Chang et al. | 585/524 |
| 6,071,864 A * | 6/2000 | Hsi Ho et al. | 508/591 |
| 6,162,757 A * | 12/2000 | Chang et al. | 502/302 |
| 6,297,180 B1 | 10/2001 | Maier | |
| 6,451,933 B1 | 9/2002 | Nagy | |
| 6,884,916 B1 * | 4/2005 | Brown et al. | 585/530 |
| 2001/0009884 A1 | 7/2001 | Moskovitz et al. | |
| 2002/0141921 A1 | 10/2002 | Wu et al. | |
| 2002/0183465 A1 | 12/2002 | Babcock et al. | |
| 2004/0011702 A1 | 1/2004 | Ma et al. | |
| 2005/0112056 A1 | 5/2005 | Hampden-Smith et al. | |
| 2005/0148744 A1 | 7/2005 | Kao | |
| 2005/0154214 A1 | 7/2005 | Heidemann et al. | |
| 2006/0060504 A1 | 3/2006 | Vierheilig | |
| 2006/0073962 A1 | 4/2006 | Murphy et al. | |
| 2007/0043250 A1 | 2/2007 | Xu et al. | |
| 2007/0090024 A1 | 4/2007 | Soled et al. | |
| 2007/0158236 A1 | 7/2007 | Zhou et al. | |
| 2007/0207918 A1 | 9/2007 | Gibson et al. | |

FOREIGN PATENT DOCUMENTS

| | | | |
|---|---|---|---|
| WO | WO 2004067586 A3 | 8/2004 | |

OTHER PUBLICATIONS

Bartels, et. al., "Lubricants and Lubrication" in Ullmann's Encyclopedia of Chemical Technology, Wiley-VCH, 2005, posted on-line Jan. 15, 2003.*

Lorz, et. al., "Phthalic Acid and Derivatives" in Ullmann's Encyclopedia of Chemical Technology, Wiley-VCH, 2005, posted on-line Jun. 15, 2007.*

Bahrmann, et al. ("Oxo Synthesis" in Ullmann's Encyclopedia of Chemical Technology, Wiley-VCH, 2005, posted on-line Jun. 15, 2000).*

Bartels, et. al. ("Lubricants and Lubrication" in Ullmann's Encyclopedia of Chemical Technology, Wiley-VCH, 2005, posted on-line Jan. 15, 2003).*

Lorz, et. al. ("Phthalic Acid and Derivatives" in Ullmann's Encyclopedia of Chemical Technology, Wiley-VCH, 2005, posted on-line Jun. 15, 2007).*

Lewis, Hawley's Condensed Chemical Dictionary, 14th ed., John Wiley & Sons, R. J. Lewis, ed., available on-line at www.knovel.com on Sep. 4, 2003.*

Spencer, Michael S. and Martyn V. Twigg, "Metal Catalyst Design and Preparation in Control of Deactivation", Annual Review of Materials Research, 2005, vol. 35, pp. 427-464.

Sugunan, S.G., G.V. Chemparathy and A. Paul, "Acid Base Characteristics of Binary Oxides of Zr with Ce and La", Indian Journal of Engineering and Materials Sciences, 1996, vol. 3, No. 1, pp. 45-47.

* cited by examiner

PROCESS FOR MAKING OLEFIN OLIGOMERS AND ALKYL BENZENES IN THE PRESENCE OF MIXED METAL OXIDE CATALYSTS

FIELD

The present disclosure relates to processes for making olefin oligomers and alkyl benzenes in the presence of mixed metal oxide catalysts.

BACKGROUND

Higher alkenes are intermediate products in the manufacture of hydrocarbon solvents, higher alcohols, aldehydes and acids. Higher olefins, i.e., those of 4 or more carbon atoms, have been conventionally produced by oligomerization of feedstreams of lighter olefins (alkenes) over homogeneous or heterogeneous acid catalysts, such as solid phosphoric acid (SPA). SPA has been widely used for this purpose. However, SPA produces significant amounts of undesirable cracked products, cannot be regenerated, and has to disposed of after it is spent. Various zeolites have also been proposed as catalysts for oligomerization of olefins.

A difficulty with use of the aforementioned oligomerization catalysts is contamination with heteroatoms, such as compounds of sulfur, nitrogen and oxygen. Contamination can result in considerable reduction in catalyst activity and selectivity. Thus, it would be desirable to have alternative catalysts for alkene oligomerization that exhibit improved heteroatom resistance.

Alkylbenzenes have been conventionally produced by alkylation of benzene with olefins in the presence of catalysts such as SPA and aluminum chloride ($AlCl_3$) as catalyst. Zeolites have also been used in many industrial processes e.g., ethyl benzene and cumene production, as catalysts for alkylation of benzene with light olefins. Zeolites are more active and selective than either SPA or $AlCl_3$. However, zeolites have the disadvantage of being more costly and are very sensitive to contamination by heteroatoms, even at very low concentrations. Contamination can be remedied by purification of feedstreams, but this is costly.

It would be desirable to have a catalyst system for processes for making olefin oligomers and alkyl benzenes. It would further be desirable to have a catalyst system that is substantially not susceptible to heteroatom contamination.

SUMMARY

According to the present disclosure, there is provided a process for oligomerizing alkenes. The process has the step of reacting (oligomerizing) an amount of one or more alkenes in the presence of a catalytically effective amount of a two or more metal oxides at a temperature effective to effect oligomerization. The two or more metal oxides are represented by the formula:

$MO_n/M'O_{n'}$ wherein M and M', are, independently, selected from the group consisting of Al, Ce, Fe, P, W, Zr, and combinations thereof; M and M' are different metals or combinations of metals; and n and n' are positive numbers and vary stoichiometrically depending on the valency of M and M', respectively.

According to the present disclosure, there is also provided a process for alkylation of an aromatic compound. The process has the step of contacting an amount of one or more alkenes with an amount of benzene in the presence of a catalytically effective amount of two or more metal oxides at a temperature effective to effect alkylation of the aromatic compound. The two or more metal oxides are as described above.

BRIEF DESCRIPTION OF DRAWINGS

To assist those of ordinary skill in the relevant art in making and using the subject matter hereof, reference is made to the appended drawings, wherein.

DETAILED DESCRIPTION

Figure 1:
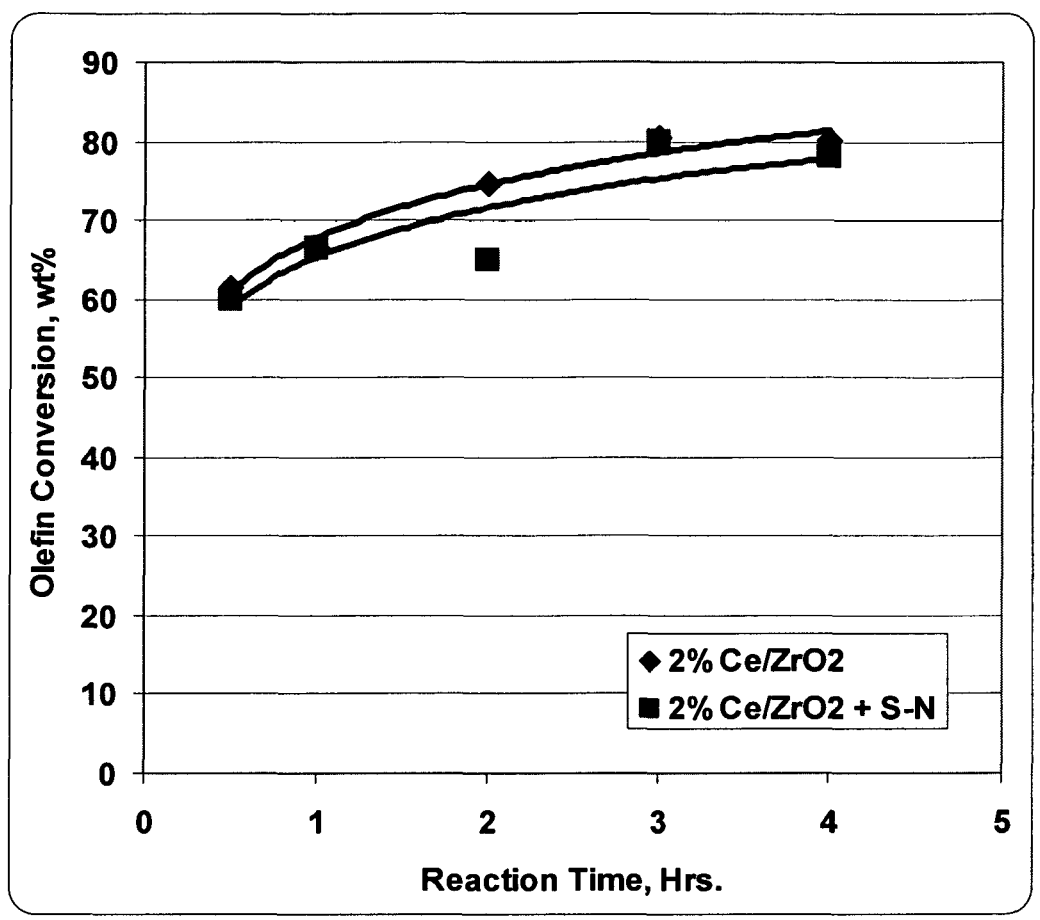
FIG. 1 is a plot of data for weight percent olefin conversion versus reaction time for Example 1.

Mixed metal oxides have been found useful as catalysts in the oligomerization of alkenes and the alkylation of benzene. All numerical values within the detailed description and the claims herein are understood as modified by "about."

Mixed metal oxides useful in the processes of the present disclosure are represented by the following formula:

$MO_n/M'O_{n'}$ wherein M and M', are, independently, selected from the group consisting of Al, Ce, Fe, P, W, Zr, and combinations thereof. M and M' are different metals or combinations of metals. "n" and "n'" are positive numbers (whole or decimal/fraction) will vary stoichiometrically depending on the valency of M and M', respectively. Useful metal oxides include $AlPO_x$, $WAlPO_x$, $WZrO_x$, $CeZrO_x$, $ZrAlPO_x$, $FeWZrO_x$ and combinations of the foregoing.

The present disclosure is useful in the oligomerization of alkenes. The presence of mixed metal oxides catalyzes the reaction such that activity (reaction rate and conversion level) and selectivity are enhanced. Useful alkenes include those having carbon atoms of from 2 to 12 carbon atoms, more advantageously 3 to 6 carbon atoms, and most advantageously 3-4 carbon atoms. Representative alkenes include propene, butenes, pentenes, hexenes, heptenes, octenes, nonenes, decenes and dodecenes or a combination of any of these olefins. A most preferred alkene is butenes. A representative oligomerization using butenes to form branched alkenes is shown in the following:

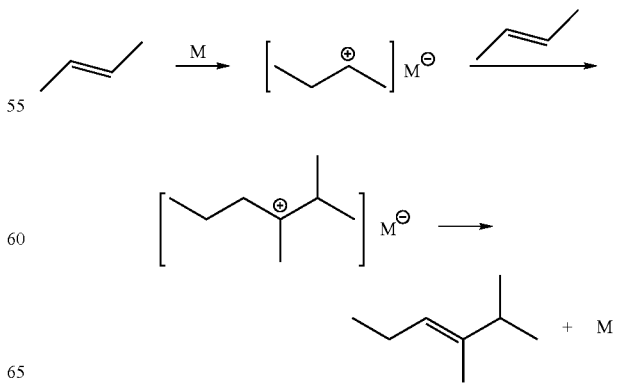

wherein M is the catalyst.

When conducting oligomerization, various reactors can be used. For example, the process can be carried out in batchwise fashion by adding the catalyst and alkene feedstock to a stirred autoclave and heating to reaction temperature. A heat transfer fluid can be circulated through the jacket of the autoclave or a condenser can be provided to maintain a constant temperature. Industrial process may employ a fixed-bed reactor operating in an upflow or downflow mode or a moving-bed reactor operating with concurrent or countercurrent catalyst and hydrocarbon flows. These reactors may contain a single catalyst bed or multiple beds and may be equipped for the interstage addition of olefins and interstage cooling. A catalytic distillation reactor configuration may also used.

In the oligomerization, the mixed metal oxides are present in a catalytically effective amount.

If desired, the olefin oligomer product may be subject to conversions or unit operations selected from the group consisting of fractionation, hydrogenation, hydroformylation, oxidation, carbonylation, esterification, etherification, epoxidation, and hydration. For example, the olefin oligomer can be hydroformulated and hydrogenated to form a higher alcohol, i.e., an alcohol having 5 to 15 carbon atoms. The higher alcohol can further be esterified via reaction with a polycarboxylic acid to make a polycarboxylic ester.

The alkenes weight hourly space velocity advantageously in the range of from 0.1 to 20, more advantageously from 1 to 10, and most advantageously from 1.1 to 7.5 weight/weight·hour.

Further in the oligomerization, the reaction is carried out at a temperature and pressure effective to effect polymerization. The temperature is advantageously from about room temperature to 300° C., more advantageously from 80° C. to 250° C., and most advantageously from 120° C. to 230° C. The pressure is advantageously at 5 to 15 MPa, more advantageously at 6 to 10 MPa, and most advantageously at 6-8 MPA pressure.

The present disclosure is also useful in the alkylation of benzene and aromatic ring derivatives. The presence of mixed metal oxides catalyzes the reaction such that activity (reaction rate and conversion level) and selectivity are enhanced. Useful alkenes include those having carbon atoms of from 2 to 12 carbon atoms, more advantageously 3 to 6 carbon atoms, and most advantageously 2-4 carbon atoms. Representative alkenes include ethylene, propylene, butenes, pentenes, hexenes, heptenes, octenes, nonenes, decenes and dodecene. A most preferred alkene is propylene and butenes. Representative product benzene derivatives include cumene, ethyl benzene, and sec-butylbenzene. A representative alkylation of benzene with butenes to produce sec-butylbenzene is shown in the following:

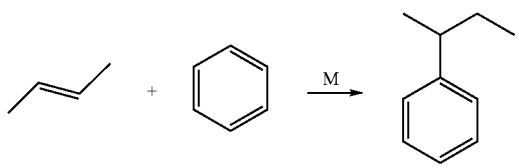

When conducting alkylation, various reactors can be used. For example, the process can be carried out in batchwise fashion by adding the catalyst and aromatic feedstock to a stirred autoclave, heating to reaction temperature, and then slowly adding the olefin feedstock. A heat transfer fluid can be circulated through the jacket of the autoclave or a condenser can be provided to maintain a constant temperature. Industrial processes may employ a fixed-bed reactor operating in an upflow or downflow mode or a moving-bed reactor operating with a concurrent or a countercurrent catalyst and hydrocarbon flows. These reactors may contain a single catalyst bed or multiple beds and may be equipped for the interstage addition of olefins and interstage cooling. A catalytic distillation reactor configuration may also be used. In the benzene alkylation reaction, the mixed metal oxides are present in a catalytically effective amount. The molar ratio of alkylatable aromatic compound to alkylating agent can be from 0.1:1 to 50:1 and advantageously from 0.5:1 to 10:1. When the alkylatable aromatic compound is benzene, the molar ratio of benzene to olefin in the reaction mode is from 5 to 30. Reaction is suitably accomplished by utilizing a feed weight hourly space velocity (WHSV) of between 0.1 $hr^{-1}$ to 100 $hr^{-1}$. The latter WHSV is based upon the total weight of active catalyst.

The alkylation process of this disclosure is conducted such that the organic reactants i.e., the alkylatable aromatic compound and the alkylating agent, are brought into contact with the catalyst in a suitable reaction zone, such as in a flow reactor containing a fixed bed of the catalyst composition under effective alkylation conditions. Such conditions include a temperature between 50° C. and 250° C. and advantageously from 125 to 200° C. The reaction generally takes place at a pressure of from 0.2 to 250 atmospheres and advantageously from 5 to 100 atmospheres.

The reaction can be in either vapor phase or liquid phase and can be neat, i.e., free from intentional admixture or dilution with other material, or the reactants can be brought into contact with the catalyst composition with the aid of carried gases or diluents, such as hydrogen or nitrogen.

Useful alkylatable aromatic compounds can be selected from the group consisting of benzene, naphthalene, anthracene, naphthalene, anthracene, phenanthrene, and phenanthrene bearing at least one substituent selected from the group consisting of alkyl, hydroxy, alkoxy, phenyl, and phenylalkyl wherein the alkyl and alkoxy groups have from 1 to 21 carbon atoms. The process is particularly useful with benzene.

Useful olefinic alkylating agents also include cycloolefins. Other useful agents alcohols and alkylhalides having from 1 up to 26 carbon atoms.

If desired, the alkyl aromatic product may optionally be oxidized to form a compound selected from the group consisting of an alcohol, a ketone, an acid, a phenol, and a ketone.

The mixed metal oxides retain a substantial degree of their catalytic effectiveness in the presence of contamination from heteroatoms and/or compounds of heteroatoms. Such heteroatoms include, but are not limited to S (sulfur), N (nitrogen), and O (oxygen). The mixed metal oxides advantageously retain 60% or more, more advantageously 70% or more, and most advantageously 80% or more of activity, i.e., conversion level on a molar basis when contaminated when compared to mixed metal oxides without contamination. The retention of catalytic effectiveness is applicable to both the oligomerization reaction and the alkylation reaction.

The following are examples of the present disclosure and are not to be construed as limiting.

EXAMPLES

Example 1

Evaluation of Ce/Zr for Resistance to Heteroatom (S—N) Effects Using 1-Butene Oligomerization in a Batch Reactor Preparation of the Catalyst Ce/Zr Employed in Example 1

Five hundred of $ZrOCl_2.8H_2O$ and fourteen grams of $Ce(SO_4)_2$ were dissolved with stirring in 3.0 liters of distilled water. Another solution containing 260 grams of concentrated $NH_4OH$ and 3.0 liters of distilled water was prepared. These two solutions were combined at the rate of 50 ml/min using nozzle mixing. The pH of the final composite was adjusted to approximately 8 by the addition of concentrated ammonium hydroxide. This slurry was then put in polypropylene bottles and placed in a steambox (100° C.) for 72 hours. The product formed was recovered by filtration, washed with excess water, and stored as a filtercake. The filtercake was dried overnight at 100° C. Thereafter the filtercake was calcined at 700° C. for a total of 3 hours in flowing air and then allowed to cool. The cerium content was analyzed as 2.6 wt %

Oligomerization Evaluation of Catalyst of Example 1:

The catalyst powder was compacted and sized to 14 to 20 mesh using a dry sieving technique prior to evaluation. The sized sample was dried at 500° F. for a minimum of 2 hours. 1.0 grams of this sized catalyst is loaded between two 0.25-inch layers of inert, 8-grit quartz particles that were previously dried at 250° F. until loaded in the stationary sample basket. The sample basket was installed in a 600 mL batch autoclave reactor containing 7.5 grams anhydrous n-decane. The batch reactor was pressure tested with $N_2$ to ensure proper sealing and absence of leaks. Pressure was reduced to ~50 pounds per square inch gauge (psig). ~200 psig $N_2$ was used to quantitatively deliver 90.0 grams of reagent grade 1-butene and 42.5 grams of reagent grade n-butane from transfer vessels to the batch reactor.

Reactor contents were mixed at 1000 rpm with a vertically positioned impeller located in the center of the stationary sample basket. The reactor was heated to 338° F. (170° C.) in 20 minutes using a programmed autoclave controller to maintain ramp rate and temperature. After reaching temperature, reactor pressure was at or near 1000 psig. If necessary, higher pressure nitrogen was added to the reactor to achieve the final target pressure of 1000 psig. Reaction time was recorded from the point at which temperature and pressure targets (170° C., 1000 psig) are attained and stable. Chromatography-sized samples of <1 mL were extracted from the reactor at intervals from 0.5 to 4 hours for off-line analysis. Only the liquid product was analyzed.

Olefin conversion, selectivity and average product branching was determined with an $H_2$-GC. This was an HP-5980 GC equipped with an autosampler and (a) a 100 meter DB-1 column (0.25 mm ID and 0.5 μm film thickness); (b) hydrogen as the carrier gas; and (c) ~0.1 g of 0.5% Pt/alumina catalyst in the GC insert of in-situ hydrogenation of the injected product. The temperature program used was the following: 2 minutes at 20° C., 8° C./minute to 275° C., and hold at 275° C. for 35 minutes. Key properties measured were defined below. Data were calculated according to the formulas below and are shown in Table 1.

Conversion=[(sum liquid product carbon species–product $C_4$–product $C_{10}$)/feed olefin content]×100.

Selectivity=[concentration carbon species/(sum liquid product carbon species–product $C_4$–product $C_{10}$)]×100.

Average Branching=0×% linear+1×% mono-branched+2×% di-branched+3×% tri-branched.

Wherein % linear+% mono-branched+% di-branched+% tri-branched=100%.

Oligomerization Evaluation of Example 1 Catalyst with Heteroatom Contaminated Feed:

A fresh portion of the 14 to 20 mesh sized Ce/Zr was dried at 500° F. for a minimum of 2 hours. 1.0 grams of this sized catalyst was loaded between two 0.25-inch layers of inert, 8-grit quartz particles that were previously dried at 250° F. until loaded in the stationary sample basket. The sample basket was installed in a 600 mL batch autoclave reactor containing 7.5 grams anhydrous n-decane blended to contain 10 wppm sulfur (from diethylsulfide) and 5 wppm nitrogen (from diethylamine). Testing continued as described in the previous section: "Oligomerization Evaluation of Example 1 Catalyst." Calculated data are shown in Table 1.

When compared to the heteroatom response of a zeolite higher olefins catalyst such as ZSM-57 (data given in Comparative Example 1), the Example 1 catalyst provides significant activity retention (see FIG. 1) while maintaining high selectivity.

Example 2

Evaluation of Ce/Zr for Resistance to Heteroatom (S—N) Effects Using 1-Butene Oligomerization in a Batch Reactor Preparation of Example 2 Catalyst Ce/Zr:

One hundred and twenty-five grams of $ZrOCl_2.8H_2O$ and nineteen grams of $Ce(SO_4)_2$ were dissolved with stirring in 1.5 liters of distilled water. Another solution containing 65 grams of concentrated $NH_4OH$ and 1.5 liters of distill water was prepared. These two solutions were combined at the rate of 50 ml/min using nozzle mixing. The pH of the final composite was adjusted to approximately 8 by the addition of concentrated ammonium hydroxide. This slurry was then put in polypropylene bottles and placed in a steambox (100° C.) for 72 hours. The product formed was recovered by filtration, washed with excess water, and stored as a filtercake. The filtercake is dried overnight at 100° C. Thereafter the filtercake is calcined at 700° C. for a total of 3 hours in flowing air and then allowed to cool. The cerium content was analyzed as 13.1%.

Oligomerization Evaluation of Example 2 Catalyst:

The catalyst powder was compacted and sized to 14 to 20 mesh using a dry sieving technique prior to evaluation. The sized sample was dried at 500° F. for a minimum of 2 hours. 1.0 grams of this sized catalyst was loaded between two 0.25-inch layers of inert, 8-grit quartz particles that were previously dried at 250° F. until loaded in the stationary sample basket. The sample basket was installed in a 600 mL batch autoclave reactor containing 7.5 grams anhydrous n-decane. The batch reactor was pressure tested with $N_2$ to ensure proper sealing and absence of leaks. Pressure was reduced to ~50 psig. ~200 psig $N_2$ was used to quantitatively deliver 90.0 grams of reagent grade 1-butene and 42.5 grams of reagent grade n-butane from transfer vessels to the batch reactor. Evaluation was conducted as described in the previous section: "Oligomerization Evaluation of Example 1 Catalyst." Calculated data are shown in Table 1.

Oligomerization Evaluation of Example 2 Catalyst with Heteroatom Contaminated Feed:

A fresh portion of the 14 to 20 mesh sized was dried at 500° F. for a minimum of 2 hours. 1.0 grams of this sized catalyst was loaded between two 0.25-inch layers of inert, 8-grit quartz particles that were previously dried at 250° F. until loaded in the stationary sample basket. The sample basket was installed in a 600 mL batch autoclave reactor containing 7.5 grams anhydrous n-decane blended to contain 10 wppm sulfur (from Diethylsulfide) and 5 wppm nitrogen (from Diethylamine). Testing continued as described in the previous section: "Oligomerization Evaluation of Example 1 Catalyst." Calculated data are shown in Table 1.

Figure 2:
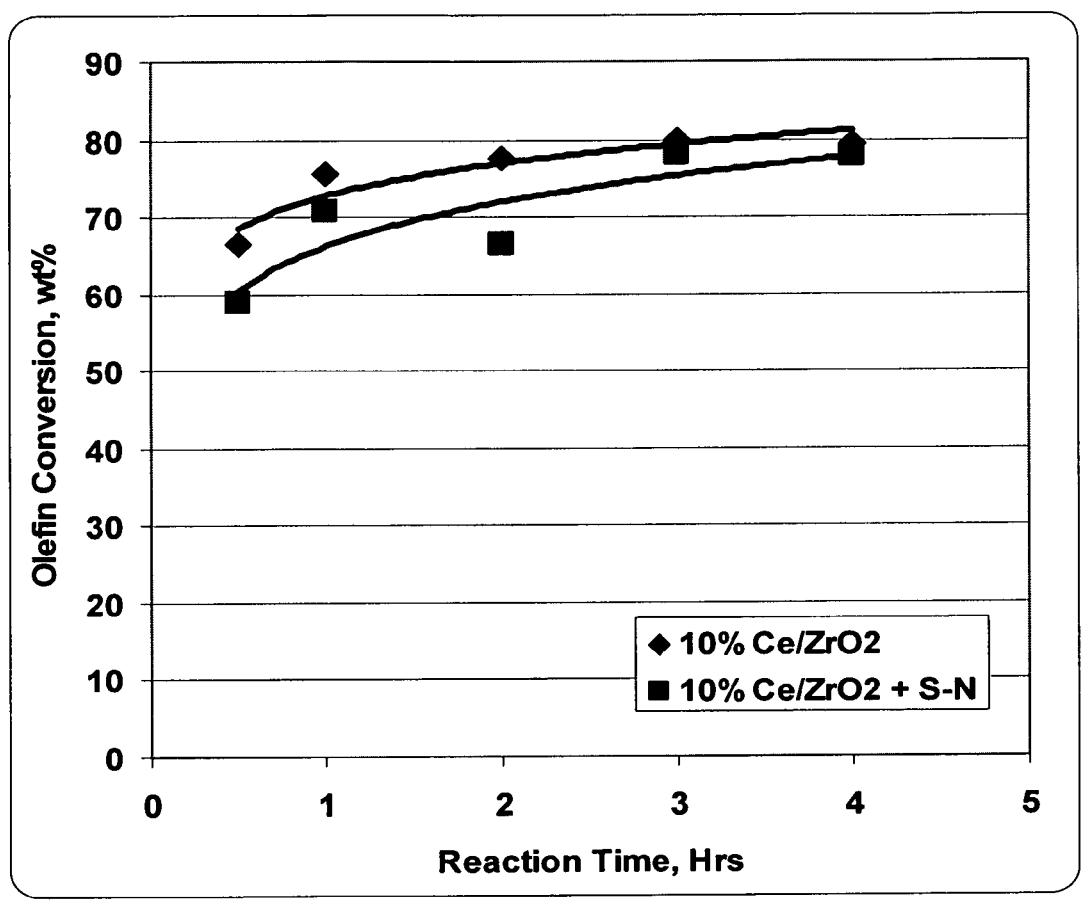
FIG. 2 is a plot of data for weight percent olefin conversion versus reaction time for Example 2.

When compared to the heteroatom response of a higher olefins catalyst such as ZSM-57 (data given as Comparative Example 1), the Example 2 catalyst provides significant activity retention (see FIG. 2) while maintaining high selectivity.

Example 3

Evaluation of WAlPO for Resistance to Heteroatom (S—N) Effects Using 1-Butene Oligomerization in a Batch Reactor Preparation of Catalyst of Example 3:

A solution (A) containing 500 grams of DI water, 45 grams of concentrated phosphoric acid, and 75 grams of concentrated sulfuric acid was prepared. Another solution (B) was prepared containing 1600 grams of DI water, 300 grams of sodium aluminate, and 35 grams of ammonium metatungstate. Solution A was added slowly to solution B with stirring. The pH was adjusted to 9 by the addition of 50% sulfuric acid solution. The gel was then placed in a polypropylene bottle and placed in a steambox (100° C.) for 48 hours. The product formed was recovered by filtration, washed with excess water, and stored as a filtercake. The filtercake was dried overnight at 100° C. Thereafter, the filtercake was calcined at 540° C. for a total of 3 hours in flowing air and then allowed to cool. The calcined material was then subjected to a total of four 1N ammonium nitrate solution exchanges. One hundred grams of ammonium nitrate solution were used per 10 grams of material. The exchanged material was dried overnight at 100° C. Thereafter the dried material as calcined at 500° C. for a total of 3 hours in flowing air. The analyses were the following: P=5.04 wt %, Al=19.1 wt %, and W=9.47 wt %.

Oligomerization Evaluation of Example 3 Catalyst:

The catalyst powder was compacted and sized to 14 to 20 mesh using a dry sieving technique prior to evaluation. The sized sample was dried at 500° F. for a minimum of 2 hours. 1.0 grams of this sized catalyst was loaded between two 0.25-inch layers of inert, 8-grit quartz particles that were previously dried at 250° F. until loaded in the stationary sample basket. The sample basket was installed in a 600 mL batch autoclave reactor containing 7.5 grams anhydrous n-decane. The batch reactor was pressure tested with $N_2$ to ensure proper sealing and absence of leaks. Pressure was reduced to ~50 psig. ~200 psig $N_2$ was used to quantitatively deliver 90.0 grams of reagent grade 1-butene and 42.5 grams of reagent grade n-butane from transfer vessels to the batch reactor. Evaluation was conducted as described in the previous section: "Oligomerization Evaluation of Example 1 Catalyst." Calculated data are shown in Table 1.

Oligomerization Evaluation of Example 3 Catalyst with Heteroatom Contaminated Feed:

A fresh portion of the 14 to 20 mesh sized was dried at 500° F. for a minimum of 2 hours. 1.0 grams of this sized catalyst was loaded between two 0.25-inch layers of inert, 8-grit quartz particles that were previously dried at 250° F. until loaded in the stationary sample basket. The sample basket was installed in a 600 mL batch autoclave reactor containing 7.5 grams anhydrous n-decane blended to contain 10 wppm sulfur (from diethylsulfide) and 5 wppm nitrogen (from diethylamine). Testing continued as described in the previous section: "Oligomerization Evaluation of Example 1 Catalyst." Calculated data are shown in Table 1.

Figure 3:
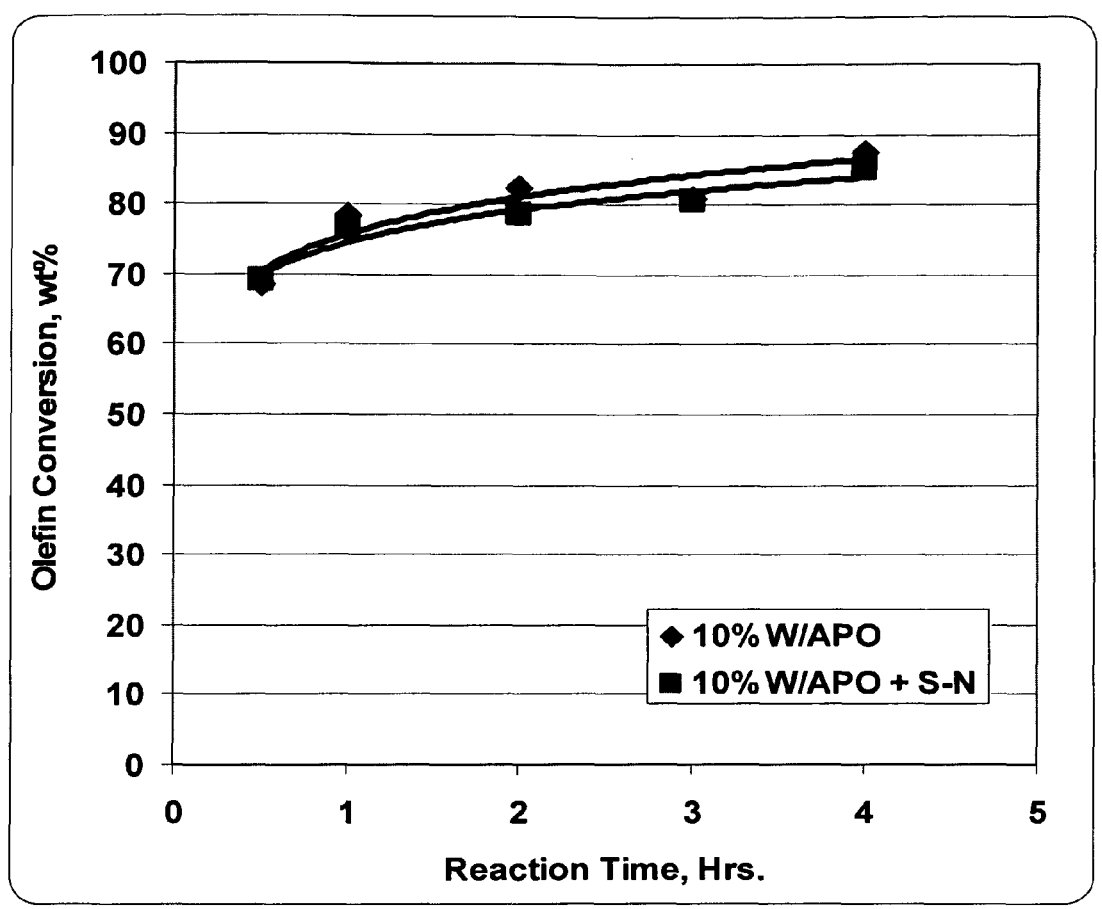
FIG. 3 is a plot of data for weight percent olefin conversion versus reaction time for Example 3.
Figure 4:
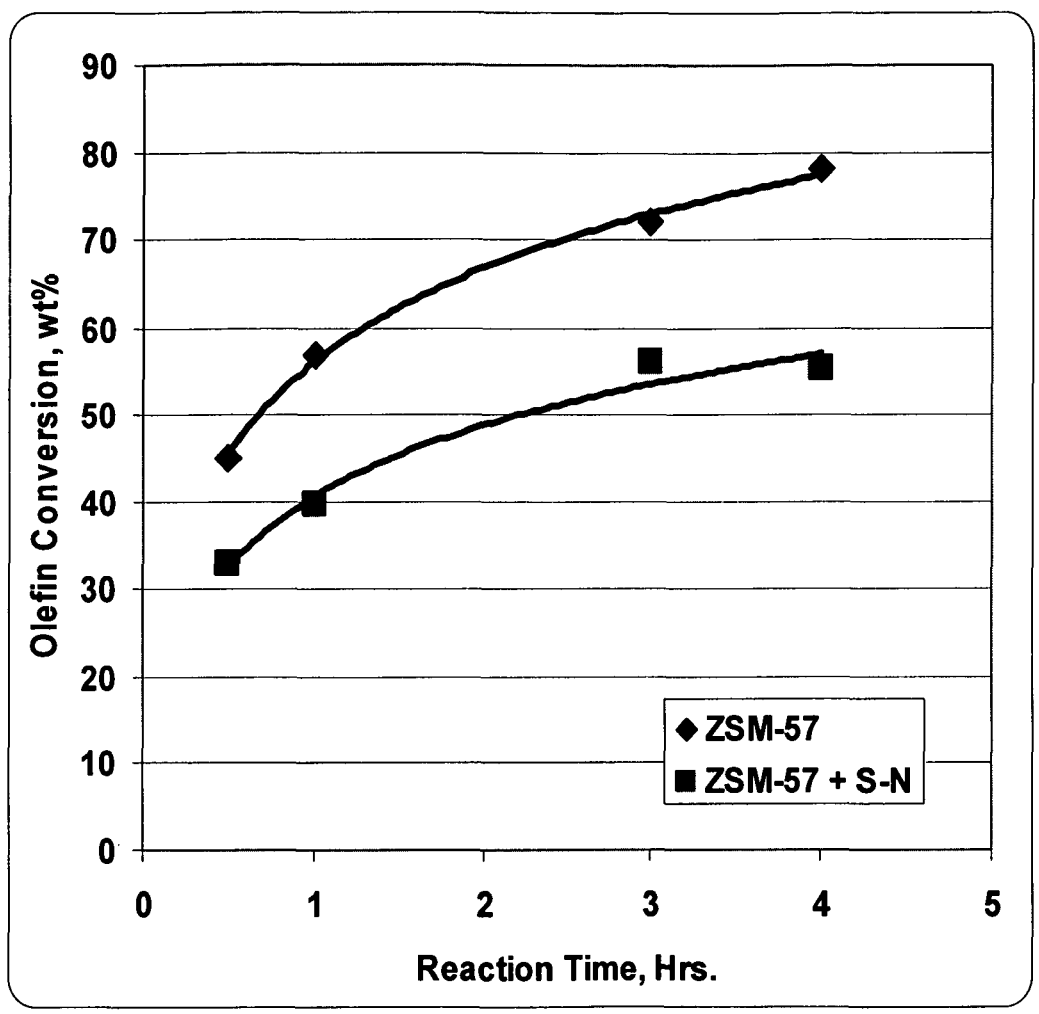
FIG. 4 is a plot of data for weight percent olefin conversion versus reaction time for Example 4.

When compared to the heteroatom response of a zeolite higher olefins catalyst such as ZSM-57 (data given in Example 4), the Example 3 catalyst provides significant activity retention (see FIG. 3) while maintaining high selectivity.

Comparative Example 1

Evaluation of Conventional ZSM-57 for Resistance to Heteroatom (S—N) Effects Using 1-Butene Oligomerization in a Batch Reactor as a Basis for Comparison Preparation of Comparative Example 1 Catalyst:

This is a sample of fresh, ZSM-57 was prepared following the recipe described in U.S. Pat. No. 7,112,711. Nominal composition is 50% zeolite and 50% Versal 300 alumina extruded to 1/10-inch.

Oligomerization Evaluation of Comparative Example 1 Catalyst:

This catalyst was dried at 500° F. for a minimum of 2 hours and analyzed without size reduction. 1.0 grams of catalyst was loaded between two 0.25-inch layers of inert, 8-grit quartz particles that were previously dried at 250° F. and loaded in the stationary sample basket. The sample basket was installed in a 600 mL batch autoclave reactor containing 7.5 grams anhydrous n-decane. The batch reactor was pressure tested with $N_2$ to ensure proper sealing and absence of leaks. Pressure was reduced to ~50 psig. 200 psig $N_2$ was used to quantitatively deliver 90.0 grams of reagent grade 1-butene and 42.5 grams of reagent grade n-butane from transfer vessels to the batch reactor. Evaluation was conducted as described in the previous section: "Oligomerization Evaluation of Example 1 Catalyst." Calculated data are shown in Table 1.

Oligomerization Evaluation of Comparative Example 1 Catalyst with Heteroatom Contaminated Feed:

A fresh portion of the ZSM-57 catalyst was dried at 500° F. for a minimum of 2 hours. 1.0 grams catalyst was loaded between two 0.25-inch layers of inert, 8-grit quartz particles that were previously dried at 250° F. and loaded in the stationary sample basket. The sample basket was installed in a 600 mL batch autoclave reactor containing 7.5 grams anhydrous n-decane blended to contain 10 wppm sulfur (from diethylsulfide) and 5 wppm nitrogen (from diethylamine). Testing continued as described in the previous section: "Oligomerization Evaluation of Example 1 Catalyst." Calculated data are shown in Table 1.

When compared to the heteroatom response of catalyst Examples 1-3, the ZSM-57 higher olefins catalyst exhibits significant activity and selectivity loss.

TABLE 1

| Sample Feed | Example 1 | | Example 2 | | Example 3 | | ZSM-57 | |
|---|---|---|---|---|---|---|---|---|
| | $C_4^=$ | $C_4^= + S + N$ | $C_4^=$ | $C_4^= + S + N$ | $C_4^=$ | $C_4^= + S + N$ | $C_4^=$ | $C_4^= + S + N$ |
| Mass, gms | 1.0 | 1.0 | 1.0 | 1.0 | 1.0 | 1.0 | 1.0 | 1.0 |
| Butene Conversion, wt % | | | | | | | | |
| 0.5 hours | 62.1 | 59.3 | 66.3 | 58.2 | 68.0 | 69.0 | 45.2 | 33.3 |
| 1.0 hours | 66.3 | 66.2 | 75.5 | 71.5 | 77.8 | 75.1 | 56.2 | 39.7 |
| 2.0 hours | 74.4 | 64.6 | 77.7 | 65.9 | 82.6 | 77.8 | NA | NA |
| 3.0 hours | 81.1 | 79.8 | 79.5 | 78.0 | 81.4 | 80.4 | 72.9 | 55.7 |
| 4.0 hours | 80.7 | 77.7 | 79.5 | 77.0 | 88.2 | 84.6 | 77.1 | 55.8 |
| Selectivity, wt % | | | | | | | | |
| $C_5$-$C_7$ | 4.74 | 5.67 | 5.85 | 5.69 | 7.23 | 8.05 | 1.05 | 1.43 |
| $C_8$ Olefins | 89.58 | 88.63 | 87.38 | 88.87 | 84.63 | 84.86 | 94.82 | 94.77 |
| $C_9$-$C_{11}$ | 4.30 | 4.74 | 4.90 | 4.42 | 5.74 | 5.75 | 1.67 | 1.70 |
| $C_{12}$ Olefins | 0.89 | 0.71 | 1.31 | 0.77 | 1.66 | 1.05 | 2.01 | 1.49 |
| $C_{12}^+$ | 1.23 | 0.69 | 1.62 | 1.12 | 1.82 | 1.16 | 0.20 | 0.25 |

Comparative Example 4

Evaluation of MCM-22 Catalyst for Benzene Alkylation with 1-Butene in a Batch Reactor (Table 2 and Table 3)

Preparation of Comparative Example 2 Catalyst (MCM-22):

This is a sample of fresh, MCM-22 was prepared following the recipe described in U.S. Pat. No. 4,954,325. Nominal composition is 65% zeolite and 35% Versal 300 alumina extruded to 1/16-inch.

Benzene Aklylation Evaluation of Comparative Example 2 (and All Examples Cited in the Present Disclosure):

The catalyst was evaluated without sizing. The sample was dried at 500° C. for a minimum of 2 hours. 1.0 grams of this sized catalyst was loaded between two 0.25-inch layers of inert, 8-grit quartz particles that were previously dried at 250° F. until loaded into the stationary sample basket. The sample basket was installed in a 600 mL batch autoclave reactor containing 7.5 grams anhydrous n-decane. The batch reactor was pressure tested with $N_2$ to ensure proper sealing and absence of leaks. Pressure was reduced to ~50 psig. ~200 psig $N_2$ was used to quantitatively deliver 120 grams of reagent grade benzene and 40 grams of reagent grade 1-butene from transfer vessels into the batch reactor.

Reactor contents were mixed at 1000 rpm with a vertically positioned impeller located in the center of the stationary sample basket. The reactor was heated to 135° C. (275° F.) in 20 minutes using a programmed autoclave controller to maintain ramp rate and temperature. After achieving temperature, reactor pressure was at or near 1000 psig. If necessary, higher pressure $N_2$ is added to the reactor to achieve the final target pressure of 1000 psig. Reaction time was recorded from the point at which temperature and pressure targets (135° C., 1000 psig) are attained and stable. The reaction period for this evaluation was 4 hours. At the end of this period, the run was discontinued, the reactor cooled to ambient conditions and the total liquid product recovered for ex-situ analysis by gas chromatography.

Product analysis by GC was based on the assumption that all components were captured in the TLP. The analysis was performed using an HP 6890 GC equipped with a DB-1 column (60M, 0.25 mm ID, 1 micrometer film thickness) and an FID detector. A microliter size portion of the product was injected onto the column and the following temperature program was used to perform the analysis: injection with 2 minute hold at −20° C., ramp at 8° C./minute to 275° C., hold at 275° C. for 35 minutes. Response factors were used to convert GC area-based data to actual composition in the product. Butene conversion was determined by measuring unreacted butene (as dissolved in the Total Liquid Product) relative to feed butene.

Example 5

Evaluation of 2% Ce/Zr Catalyst for Benzene Alkylation with 1-Butene in a Batch Reactor (Table 2)

Preparation of Example Catalyst 4:

Five hundred grams of $ZrOCl_2.8H_2O$ and 14 grams of $Ce(SO_4)_2$ were dissolved with stirring in 3.0 liters of distilled water. Another solution containing 260 grams of concentrated $NH_4OH$ and 3.0 liters of distill water was prepared. These two solutions were combined at the rate of 50 ml/min using a nozzle mixing. The pH of the final composite was adjusted to approximately 8 by the addition of concentrated sulfuric acid. This slurry was then put in polypropylene bottles and placed in a steambox (100° C.) for 72 hours. The product formed was recovered by filtration, washed with excess water, and stored as a filtercake. The filtercake was dried overnight at 100° C. Thereafter the filtercake was calcined at 700° C. for a total of 3 hours in flowing air and then allowed to cool. The cerium content was analyzed as 2.86%.

Benzene Aklylation Evaluation of Example Catalyst 5:

Same technique as for Comparative Example 2 above.

Example 6

Evaluation of $WAlPO_z$ Catalyst for Benzene Alkylation with 1-Butene in a Batch Reactor (Run 18 in Table 2)

Preparation of Example Catalyst 6:

One solution (A) was prepared by combining, with stirring, 500 grams of DI water, 45 grams of phosphoric acid (85%), and 75 grams of concentrated sulfuric acid. Another solution (B) was prepared by combining, with stirring, 1600 grams of DI water, 300 grams of sodium aluminate, $NaAlO_2$, and 35 grams of ammonium meta tungstate, $(NH_4)_6$ $H_2W_{12}O_{39} \cdot xH_2O$ (66.9% W). Solution A was then slowly added, with stirring, to solution B. The pH of the combined mixture was then adjusted to 9 by the addition of 50% sulfuric acid (92 grams). This slurry was then put in polypropylene bottles and placed in a steambox (100° C.) for 48 hours. The product formed was recovered by filtration, washed with excess water, and stored as a filtercake. The filtercake is dried overnight at 100° C. The elemental analyses were aluminum, 19.1 weight %, phosphorous, 5.0 weight %, and tungsten, 9.47 weight %. Thereafter the filtercake was calcined at 540° C. for a total of 3 hours in flowing air and then allowed to cool. The calcined product was then subjected to four separate ammonium nitrate (1N) solution exchanges (100 ml of solution per 10 grams of calcined product). Finally, the exchanged product was calcined in air to 500° C. for a total of 3 hours in flowing air and then allowed to cool.

Benzene Aklylation Evaluation of Example Catalyst 6:
  Same technique as for Comparative Example 2 above.

Example 7

Evaluation of 1% Fe/16% W/Zr Catalyst for Benzene Alkylation with 1-Butene in a Batch Reactor (Tables 2 and 3)

Preparation of Catalyst Example 7:

Five hundred grams of $ZrOCl_2 \cdot 8H_2O$ and 7.6 grams of $Fe(SO_4)$ 7 $H_2O$ were dissolved with stirring in 3.0 liters of distilled water. Another solution containing 260 grams of concentrated $NH_4OH$, 54 grams of $(NH_4)_6H_2W_{12}O_{39} \cdot xH_2O$ (66.9% W) and 3.0 liters of distill water was prepared. These two solutions were combined at the rate of 50 ml/min using a nozzle mixing. The pH of the final composite was adjusted to approximately 9 by the addition of concentrated $NH_4OH$. This slurry was then put in polypropylene bottles and placed in a steambox (100° C.) for 72 hours. The product formed was recovered by filtration, washed with excess water, and stored as a filtercake. The filtercake was dried overnight at 100° C. Thereafter the filtercake was calcined at 800° C. for a total of 3 hours in flowing air and then allowed to cool. The elemental analyses were Fe, 0.65 weight %, W, 18.2 weight %, and Zr, 55.2 weight %.

Benzene Aklylation Evaluation of Example Catalyst 7:
  Same technique as for Comparative Example 2 above.

Example 8

Evaluation of $ZrAlPO_x$ Catalyst for Benzene Alkylation with 1-Butene in a Batch Reactor (Table 2)

Preparation of Catalyst Example 8:

One solution (A) was prepared by combining, with stirring, 500 grams of DI water, 29 grams of phosphoric acid (85%), and 235 grams of $ZrOCl_2 \cdot 8H_2O$. Another solution (B) was prepared by combining, with stirring, 1200 grams of DI water and 170 grams of sodium aluminate, $NaAlO_2$. Solution A was then slowly added, with stirring, to solution B. The pH of the combined mixture was then adjusted to 9 by the addition of 50% sulfuric acid (20 grams). This slurry was then put in polypropylene bottles and placed in a steambox (100° C.) for 48 hours. The product formed was recovered by filtration, washed with excess water, and stored as a filtercake. The filtercake was dried overnight at 100° C. The elemental analyses were aluminum, 13.2 weight %, phosphorous, 3.1 weight %, and zirconium, 41.6 weight %. Thereafter, the filtercake was calcined at 540° C. for a total of 3 hours in flowing air and then allowed to cool. The calcined product was then subjected to four separate ammonium nitrate (1N) solution exchanges (100 ml of solution per 10 grams of calcined product). Finally the exchanged product was calcined in air to 500° C. for a total of 3 hours in flowing air and then allowed to cool.

Benzene Aklylation Evaluation of Example Catalyst 8:
  Same technique as for Comparative Example 2 above.

Results shown in Table 2 are based on product distributions using feed without sulfur contaminates. Of the catalysts evaluated, example catalyst #7 exhibited significantly increased butene conversion versus commercial MCM-22 used as base case for these comparisons. In addition, it shows alkylbenzene productions that are significantly higher than other examples provided. Most notably, catalyst #7 also shows a 3.5-fold increase in di-butylbenzene while maintaining roughly 60% of the sec-butylbenzene production versus MCM-22. Example 5 illustrates the impact of higher temperature operation in an attempt to increase alkylbenzene produced.

TABLE 2

Comparison of 1-Butene Conversion Products in Batch Reactor

| | Example # | | | | | |
|---|---|---|---|---|---|---|
| | 4 | 5 | 5 | 6 | 7 | 8 |
| catalyst | MCM-22 | 2% Ce/ZrO2 | 2% Ce/ZrO2 | 5% W15% Al 10% P | 1% Fe/16% W/ZrO2 | Zr/AlPO |
| Temperature ° C. | 135 | 135 | 170 | 135 | 135 | 135 |
| Butene conv. Wt % | 39 | 7.4 | 12.4 | 19.1 | 89.8 | 7.5 |
| Product Selectivity wt % | | | | | | |
| Iso-butylene | 0.12 | 5.46 | 3.10 | 10.92 | 0.01 | 28.20 |
| C5-7 olefins | 0.25 | 9.83 | 5.53 | 11.47 | 0.42 | 18.27 |
| C8, C12 olefins | 5.15 | 46.24 | 46.31 | 5.05 | 12.73 | 11.94 |
| tert butyl benzene | 0.01 | 0.23 | 0.20 | 0.37 | 0.05 | 0.83 |

TABLE 2-continued

Comparison of 1-Butene Conversion Products in Batch Reactor

| | Example # | | | | | |
|---|---|---|---|---|---|---|
| | 4 | 5 | 5 | 6 | 7 | 8 |
| Sec-butyl benzene | 85.96 | 34.87 | 40.60 | 0.23 | 50.62 | 27.12 |
| Di-butyl benzene | 7.97 | 1.50 | 3.10 | 000 | 27.07 | 8.24 |
| Tri-butyl benzene | 0.45 | 1.10 | 0.50 | 00 | 7.02 | 3.01 |
| Heavies | 0.10 | 0.81 | 0.62 | 71.6 | 1.67 | 2.41 |

Reaction conditions: 120 gr benzene, 40 gr 1-butene, pressure 1000 PSIG, Impeller speed 1000 RPM Results shown in Table 3 compare the impact of sulfur contaminates on alkylbenzene produced by the catalysts evaluated. The data show that feed spiked with 10 ppm sulfur compounds resulted in complete deactivation of the alkylation activity using MCM-22. In contrast, MMO did not show significant deactivation when compared to MCM-22.

TABLE 3

Comparison of Effect of Sulfur on 1-Butene Conversion Products in Batch Reactor

| | Example # | |
|---|---|---|
| | 7 | 7 |
| catalyst | 1% Fe/16% W/ZrO2 | 1% Fe/16% W/ZrO2* |
| Temperature ° C. | 135 | 135 |
| Butene conv. Wt % | 89.8 | 71.8 |
| Iso-butylene | 0.01 | 0.09 |
| C5-7 olefins | 0.42 | 0.46 |
| C8, C12 olefins | 12.73 | 15.83 |
| tert butyl benzene | 0.05 | 0.03 |
| Sec-butyl benzene | 50.62 | 51.07 |
| Di-butyl benzene | 27.07 | 24.456 |
| Tri-butyl benzene | 7.02 | 6.16 |
| Heavies | 1.67 | 1.36 |

Reaction conditions: 120 gr benzene, 40 gr 1-butene, pressure 1000PSIG, Impeller speed 1000 RPM
*10 ppm sulfur from diethyl sulfide was mixed with the feed.

Applicants have attempted to disclose all embodiments and applications of the disclosed subject matter that could be reasonably foreseen. However, there may be unforeseeable, insubstantial modifications that remain as equivalents. While the present invention has been described in conjunction with specific, exemplary embodiments thereof, it is evident that many alterations, modifications, and variations will be apparent to those skilled in the art in light of the foregoing description without departing from the spirit or scope of the present disclosure. Accordingly, the present disclosure is intended to embrace all such alterations, modifications, and variations of the above detailed description.

All patents, test procedures, and other documents cited herein, including priority documents, are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated.

What is claimed is:

1. A process for making an olefin oligomer from a contaminated olefinic feedstock, comprising: oligomerizing an amount of one or more olefins in the presence of a catalyst comprising a catalytically effective amount of two or more metal oxides at a temperature effective to effect oligomerization, wherein the catalyst is represented by the formula:

$$MO_n/M'O_{n'}$$

wherein M and M', are selected from the group consisting of Al, Ce, Fe, P, W, Zr, and combinations thereof; M and M' are different metals or combinations of metals; n and n' are positive numbers and vary stoichiometrically depending on the valency of M and M', respectively, wherein the contaminated olefinic feedstocks include at least 5 wppm of one or more organic compounds which contain one or more heteroatoms wherein the heteroatoms are chosen from sulfur, nitrogen, oxygen and combinations thereof, and wherein the two or more metal oxides retain 60% or more activity compared to metal oxides without contamination, and wherein the two or more metal oxides are prepared by co-precipitation and calcined in an oxidizing environment prior to the oligomerizing step.

2. The process of claim 1, wherein the two or more metal oxides are selected from the group consisting of $AlPO_x$, $WAlPO_x$, $ZrO_2$, $ZrAlPO_x$, $CeO_2$, $WZrO_x$, $FeWZrO_x$, $CeZrO_x$ and combinations of the foregoing, wherein x is a positive number and varies stoichiometrically depending on the valency of other elements included within the metal oxide.

3. The process of claim 1, wherein the one or more olefins has from 3 to 12 carbon atoms.

4. The process of claim 1, wherein the one or more olefins is butenes.

5. The process of claim 1, wherein the oligomerization is carried out at a temperature from 25° C. to 300° C.

6. The process of claim 1, wherein the catalyst includes a mixture of more than one catalyst with each catalyst comprising two or more metal oxides.

7. The process of claim 1, wherein the alkenes weight hourly space velocity is from 0.1 to 20 weight/weight·hour.

8. The process of claim 1, wherein the alkenes weight hourly space velocity is from 1 to 10 weight/weight·hour.

9. The process of claim 1, wherein the alkenes weight hourly space velocity is from 1.1 to 7.5 weight/weight·hour.

10. The process according to claim 1, further comprising subjecting the olefin oligomer to one or more steps selected from the group consisting of fractionation, hydrogenation, hydroformylation, oxidation, carbonylation, esterification etherification, epoxidation, and hydration.

11. The process according to claim 10, further comprising hydroformylating the olefin oligomer to form an aldehyde and hydrogenating the aldehyde to form a higher alcohol.

12. The process according to claim 11, further comprising reacting the higher alcohol with a polycarboxylic acid to make a polycarboxylic ester.

13. The process of claim 1, wherein the two or more metal oxides retain 80% or more activity compared to metal oxides without contamination.

14. A process for making an alkyl aromatic compound from a contaminated olefinic feedstock and/or a contaminated alkylaromatic feedstock, comprising: contacting an amount of one or more olefins with an amount of an alkylatable aromatic compound in the presence of a catalyst comprising a catalytically effective amount of two or more metal oxides at a temperature effective to effect alkylation, wherein the catalyst is represented by the formula:

$$MO_n/M'O_{n'}$$

wherein M is selected from the group consisting of Al, Ce, Fe, and P, and combinations thereof and M' is selected from the group consisting of Al, Ce, Fe, P, W, Zr, and combinations thereof; M and M' are different metals or combinations of metals; n and n' are positive numbers and vary stoichiometrically depending on the valency of M and M', respectively,
wherein the contaminated olefinic and/or alkylaromatic feedstocks include at least 5 wppm of one or more organic compounds which contain one or more heteroatoms wherein the heteroatoms are chosen from sulfur, nitrogen, oxygen and combinations thereof, and
wherein the two or more metal oxides retain 60% or more activity compared to oxides without contamination, and
wherein the two or more metal oxides are prepared by co-precipitation and calcined an oxidizing environment prior to the alkylation step.

15. The process of claim 14, wherein the two or more metal oxides are selected from the group consisting of $AlPO_x$, $WAlPO_x$, $ZrO_2$, $ZrAlPO_x$, $CeO_2$, $FeWZrO_x$, $CeZrO_x$, and combinations of the foregoing,
wherein x is a positive number and varies stoichiometrically depending on the valency of other elements included within the metal oxide.

16. The process of claim 14, wherein the one or more olefins has from 2 to 12 carbon atoms.

17. The process of claim 14, WHEREIN the one or more olefins are ethylene, propylene and/or butenes.

18. The process of claim 14, wherein the alkylation is carried out at a temperature from 70° C. to 240° C.

19. The process of claim 14, wherein two or more metal oxides are present from 0.1 to 100 wt % based on the weight of the one or more olefins.

20. The process of claim 14, wherein the alkylatable aromatic compound is benzene, and wherein the molar ratio of benzene to olefin in the reaction mode is from 1 to 30.

21. The process of claim 14, wherein the alkylatable aromatic compound is selected from the group consisting of benzene, naphthalene, anthracene, phenanthrene, and bearing at least one substituent selected from the group consisting of alkyl, hydroxy, alkoxy, phenyl, and phenylalkyl wherein the alkyl and alkoxy groups have 1 to 21 carbon atoms.

22. The process of claim 14, wherein the alkylating agent is selected from the group consisting of an olefin, a cyclo olefin, an alcohol, or an alkylhalide having from 1 up to 26 carbon atoms.

23. The process of claim 14, wherein the alkylation is carried out at a pressure from 5 to 100 atmospheres.

24. The process of claim 14, further comprising oxidizing the alkyl aromatic to form a compound selected from the group consisting of an alcohol, a ketone, an acid, and a phenol.

25. The process of claim 14, wherein the two or more metal oxides retain 80% or more activity compared to metal oxides without contamination.

* * * * *